(12) United States Patent
Dunning (10) Patent No.: US 8,388,614 B2
(45) Date of Patent: Mar. 5, 2013

(54) RETURN ELECTRODE TEMPERATURE PREDICTION

(75) Inventor: James E. Dunning, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 686 days.

(21) Appl. No.: 12/569,610

(22) Filed: Sep. 29, 2009

(65) Prior Publication Data

US 2011/0077641 A1   Mar. 31, 2011

(51) Int. Cl.
A61B 18/04 (2006.01)

(52) U.S. Cl. .......................... 606/34; 606/35

(58) Field of Classification Search ........... 606/32, 606/34, 35; 607/152
See application file for complete search history.

(56) References Cited

U.S. PATENT DOCUMENTS

| | | | |
|---|---|---|---|
| 4,416,276 A * | 11/1983 | Newton et al. | 606/35 |
| 4,416,277 A * | 11/1983 | Newton et al. | 606/35 |
| 5,496,312 A * | 3/1996 | Klicek | 606/34 |
| 5,660,892 A | 8/1997 | Robbins et al. | |
| 5,698,455 A | 12/1997 | Meikle et al. | |
| 5,755,715 A | 5/1998 | Stern et al. | |
| 5,763,837 A | 6/1998 | Davignon et al. | |
| 6,032,063 A | 2/2000 | Hoar et al. | |
| 6,063,075 A | 5/2000 | Mihori | |
| 6,114,706 A | 9/2000 | Meikle et al. | |
| 6,258,085 B1 * | 7/2001 | Eggleston | 606/35 |
| 6,565,559 B2 * | 5/2003 | Eggleston | 606/35 |
| 6,625,702 B2 | 9/2003 | Rentschler et al. | |
| 7,137,980 B2 * | 11/2006 | Buysse et al. | 606/34 |
| 7,160,293 B2 * | 1/2007 | Sturm et al. | 606/35 |
| 7,258,688 B1 * | 8/2007 | Shah et al. | 606/34 |
| 7,306,593 B2 | 12/2007 | Keidar et al. | |
| 8,231,614 B2 * | 7/2012 | Dunning et al. | 606/32 |
| 2003/0125983 A1 | 7/2003 | Flack et al. | |
| 2006/0079872 A1 * | 4/2006 | Eggleston | 606/35 |
| 2008/0281310 A1 * | 11/2008 | Dunning et al. | 606/32 |
| 2008/0281311 A1 * | 11/2008 | Dunning et al. | 606/32 |
| 2009/0036884 A1 * | 2/2009 | Gregg et al. | 606/35 |
| 2012/0109121 A1 * | 5/2012 | Gregg | 606/35 |

FOREIGN PATENT DOCUMENTS

| | | |
|---|---|---|
| CA | 1219642 | 3/1987 |
| DE | 3206947 | 9/1983 |
| DE | 3544443 | 6/1987 |
| DE | 4238263 | 5/1993 |
| DE | 4231236 | 3/1994 |
| DE | 19717411 | 11/1998 |
| DE | 19801173 | 7/1999 |
| DE | 10328514 | 6/2003 |
| DE | 102004010940 | 9/2005 |

(Continued)

OTHER PUBLICATIONS

U.S. Appl. No. 10/609,946, filed Jun. 30, 2003.

(Continued)

*Primary Examiner* — Linda Dvorak
*Assistant Examiner* — Jocelyn D Ram (57) ABSTRACT

The present disclosure relates to an electrosurgical generator for supplying electrosurgical energy to tissue and methods thereof. The electrosurgical generator includes sensor circuitry, a processing device, and a controller. The type of return electrode pad may be determined automatically. The sensor circuitry is configured to determine one or more characteristics of a patient and/or measure tissue temperature at a return electrode pad site. The processing device is configured to determine a maximum temperature of tissue and calculate real-time predicted temperature at the return electrode pad site. The controller is configured to regulate output of the electrosurgical generator based on one or more characteristics of a patient and the determined maximum temperature.

6 Claims, 7 Drawing Sheets

FOREIGN PATENT DOCUMENTS

| | | |
|---|---|---|
| EP | 0262888 | 4/1988 |
| EP | 390937 | 10/1990 |
| EP | 836868 | 4/1998 |
| EP | 0930048 | 7/1999 |
| EP | 1051949 | 11/2000 |
| EP | 1076350 | 2/2001 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| FR | 2276027 | 6/1974 |
| FR | 2516782 | 5/1983 |
| GB | 2054382 | 2/1981 |
| GB | 2374532 | 10/2002 |
| WO | WO 00/65993 | 11/2000 |
| WO | WO 2005/087124 | 9/2005 |
| WO | WO 2005/115262 | 12/2005 |
| WO | WO 2008/009385 | 1/2008 |

OTHER PUBLICATIONS

U.S. Appl. No. 11/900,190, filed Sep. 10, 2007.
U.S. Appl. No. 12/396,814, filed Mar. 3, 2009.
U.S. Appl. No. 12/395,812, filed Mar. 2, 2009.
U.S. Appl. No. 12/364,624, filed Feb. 3, 2009.
U.S. Appl. No. 12/355,281, filed Jan. 16, 2009.
U.S. Appl. No. 12/401,428, filed Mar. 10, 2009.
U.S. Appl. No. 12/407,008, filed Mar. 19, 2009.
U.S. Appl. No. 12/569,610, filed Sep. 29, 2009.
Boyles, Walt; "Instrumentation Reference Book", 2002; Butterworth-Heinemann; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779—partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
International Search Report PCT/US04/04196 dated Jan. 6, 2005.

* cited by examiner

RETURN ELECTRODE TEMPERATURE PREDICTION

BACKGROUND

1. Technical Field

The present disclosure relates to an electrosurgical apparatus, system and method. More particularly, the present disclosure is directed to an algorithm configured to predict temperature performance of a return electrode pad placed on a patient during electrosurgical procedures.

2. Background of Related Art

Energy-based tissue treatment is well known in the art. Various types of energy (e.g., electrical, ultrasonic, microwave, cryogenic, heat, and laser) are applied to tissue to achieve a desired result. Electrosurgery involves application of high radio frequency electrical current to a surgical site to cut, ablate, coagulate or seal tissue. In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode.

The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

Accordingly, during electrosurgery, it is necessary to have the capability to monitor current, impedance, and/or temperature at the return electrode pad site and regulate current, impedance, and/or temperature at the electrosurgical site.

SUMMARY

The present disclosure relates to an electrosurgical generator for supplying electrosurgical energy to tissue. The electrosurgical generator includes sensor circuitry, a processing device, and a controller. The type of return electrode pad may be determined automatically. The sensor circuitry is configured to determine one or more characteristics of a patient and measure tissue temperature at a return electrode pad site. The processing device is configured to determine a maximum temperature of tissue at the return electrode pad site. The controller is configured to regulate output of the electrosurgical generator based one or more characteristics of a patient and the determined maximum temperature.

In some embodiments, the processing device may be configured to calculate the maximum temperature based on the one or more characteristics of a patient and an impedance value of one or more electrodes. In other embodiments, the controller may be configured to adjust the output of the electrosurgical generator to a predetermined level based on the determined maximum temperature.

In some embodiments, variables from a look-up table may be loaded into the electrosurgical generator and automatically adjust the energy based on the type of return electrode pad. The characteristics of the patient may be, for example, sex, body weight, body mass index, and body fat percentage.

The present disclosure also relates to a method for calculating a maximum temperature at a return electrode pad site. The method includes the steps of: determining one or more characteristics of a patient and calculating a constant relative to patient tissue type; calculating a maximum temperature utilizing the constant relative to patient tissue type at the return electrode pad site; applying energy to tissue at a surgical site; measuring a real-time temperature of tissue at the return electrode pad site and calculating a difference between the real-time temperature and the maximum temperature; and adjusting the energy according to the difference between the real-time temperature and the maximum temperature.

In some embodiments, the method may also include the step of determining a type of a return electrode pad adapted to be placed on tissue at the return electrode pad site based on the constant relative to patient tissue type.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for a system and method for monitoring and calculating a maximum temperature of a return electrode pad. The method includes an algorithm, as will be discussed in greater detail below that utilizes energy tracking and/or temperature predicting to monitor a safe temperature (i.e., maximum temperature) at a return electrode pad site. The method monitors the current level and activation time of the return electrode pad to predict the maximum temperature the return electrode pad site or tissue can safely handle. Based on the predicted (i.e., calculated) maximum temperature, an alarm, warning, or any other suitable alerting technique may be used to notify a clinician if a surgical condition at the return electrode pad site has become unsafe. In other words, if the tissue at the return electrode pad has reached a temperature that is above the maximum temperature or an unsafe temperature.

Figure 1:
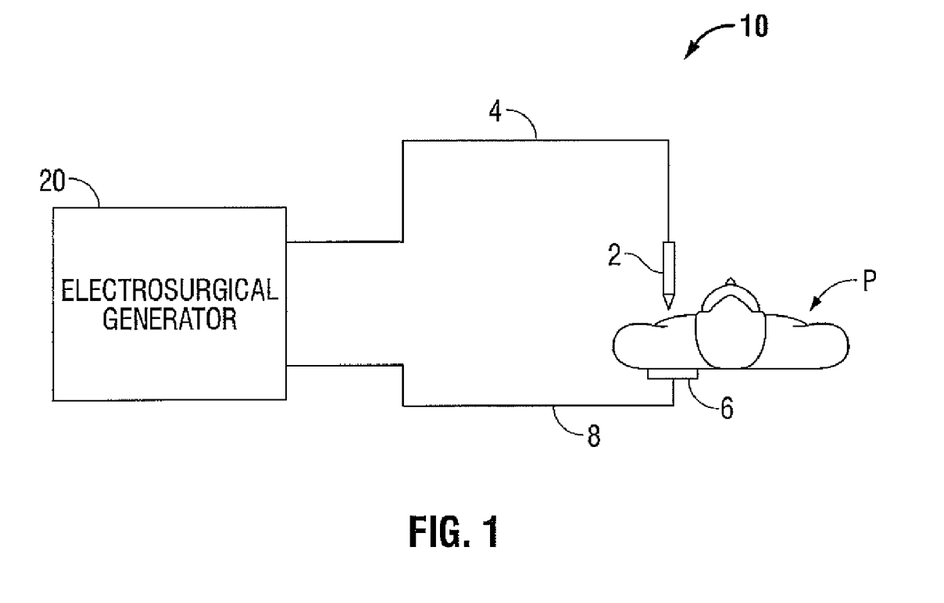
FIG. 1 is a schematic block diagram of an electrosurgical system according to one embodiment of the present disclosure.

FIG. 1 is a schematic illustration of an electrosurgical system 10 according to one embodiment of the present disclosure. The system 10 includes an electrosurgical instrument 2, which is a monopolar instrument including one or more active electrodes (e.g., electrosurgical cutting probe, and ablation electrode(s)) for treating tissue of a patient P. Electrosurgical RF energy is supplied to the instrument 2 by a generator 20 via an electrosurgical cable 4 connected to an active output terminal that allows the instrument 2 to coagulate, ablate and/or otherwise treat tissue. The energy is returned to the generator 20 through a return electrode pad 6 via a return cable 8. The system 10 may include a plurality of return electrodes pads 6 arranged to minimize the chances of tissue damage by maximizing the overall contact area with the patient P. In addition, the generator 20 and the return electrode 6 may be configured for monitoring so-called "tissue-to-patient" contact to ensure that sufficient contact exists therebetween to further minimize chances of tissue damage.

The generator 20 may include input controls (e.g., buttons, activators, switches, and touch screens) for controlling the generator 20. In addition, the generator 20 may include one or more display screens for providing the clinician with a variety of output information (e.g., intensity settings and treatment complete indicators). The input controls (not shown) allow the clinician to adjust power of the RF energy, waveform, and other parameters to achieve the desired electrosurgical output suitable for a particular task (e.g., coagulating and cauterizing). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2:
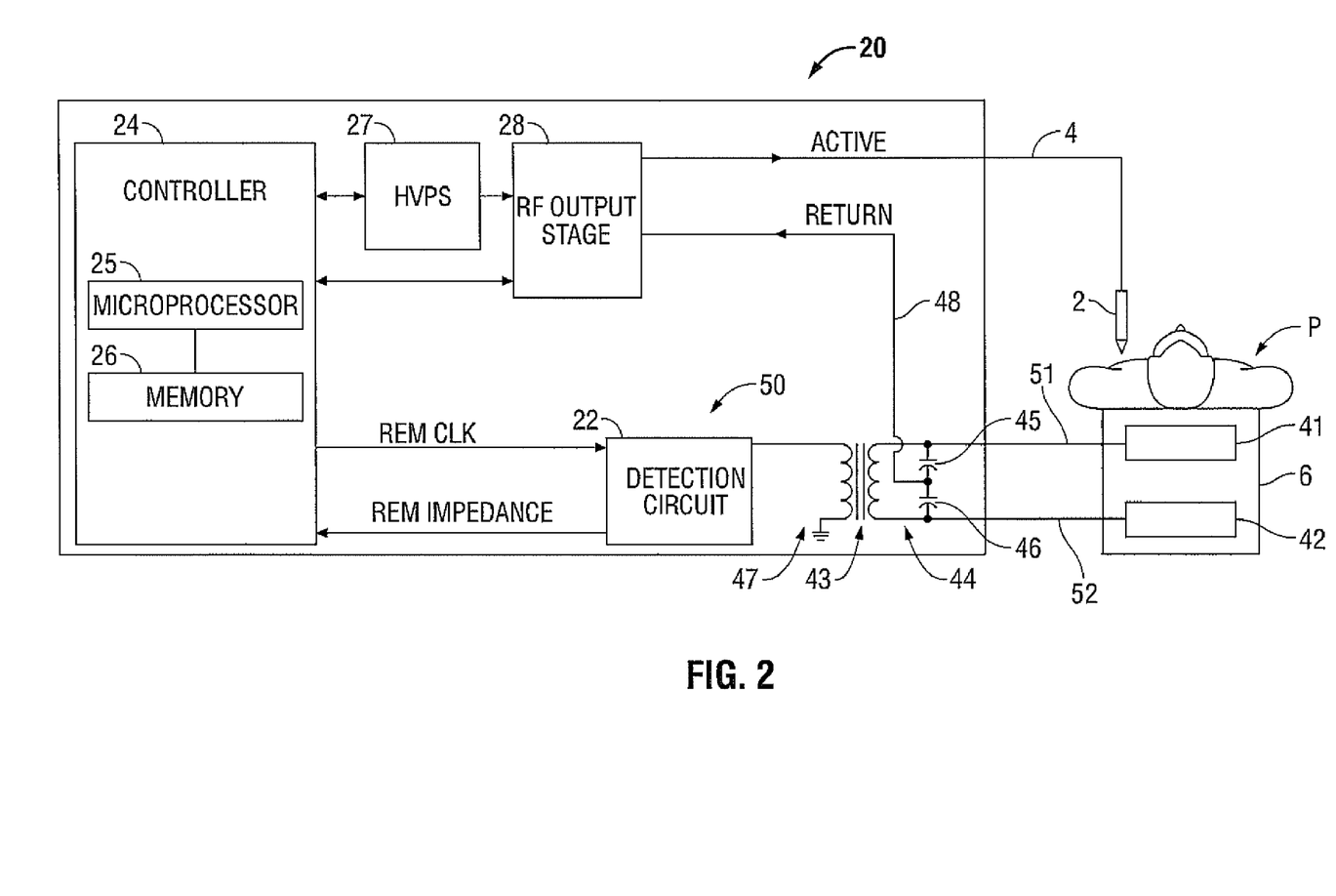
FIG. 2 is a schematic block diagram of a generator according to another embodiment of the present disclosure.

FIG. 2 shows a schematic block diagram of an exemplary embodiment of the generator 20 having a controller 24, a high voltage DC power supply 27 (HVPS) and an RF output stage 28. The HVPS 27 provides high voltage DC power to an RF output stage 28, which then converts high voltage DC power into RF energy and delivers the RF energy to the active electrode. In particular, the RF output stage 28 generates suitable waveforms of high RF energy. The RF output stage 28 is configured to generate a plurality of waveforms having various duty cycles, peak voltages, crest factors, and other parameters.

The controller 24 includes a microprocessor 25 operably and logically connected to a memory 26, which may be volatile type memory (e.g., RAM) and/or non-volatile type memory (e.g., flash media, disk media, and EPROM). The microprocessor 25 includes an output port that is operably and logically connected to the HVPS 27 and/or RF output stage 28 that allows the microprocessor 25 to control the output of the generator 20 according to either open and/or closed control loop schemes. Those skilled in the art will appreciate that the microprocessor 25 may be substituted by any logic processor (e.g., a control circuit) adapted to perform the calculations discussed herein.

The generator 20 includes a return electrode monitoring ("REM") system 50 having a detection circuit 22 that is coupled to a pair of split electrode pads, a first electrode pad 41 and a second electrode pad 42 disposed within the return electrode pad 6. The return electrode pad 6 is in contact with the patient P and returns the electrosurgical energy to the generator 20 via the first and second electrode pads 41 and 42 coupled to leads 51 and 52, respectively. In one embodiment, the return electrode pad 6 may include a plurality of split electrode pads arranged in pairs that are coupled to a corresponding number of leads. The leads 51 and 52 are enclosed in a return cable 8 and are terminated at a secondary winding 44 of a transformer 43. The leads 51 and 52 are interconnected by capacitors 45 and 46. A return lead 48 is coupled between the capacitors 45 and 46 and is adapted to return the electrosurgical energy to the RF output stage 28. The transformer 43 of the REM system 50 also includes a primary winding 47 that is connected to the detection circuit 22.

The controller 24 provides a drive signal, REM CLK, at a specific interrogation frequency to the detection circuit 22. REM CLK, is a clock signal generated by the controller 24 at the specific frequency, which may be either a square wave, a sine wave, an impulse or step signal. REM CLK may be a constant, physiologically benign waveform (e.g., 140 kHz, 2 mA) that the detection circuit 22 applies to the first electrode pad 41. The drive signal thereafter passes through the patient and is returned to the circuit 22 via the second electrode pad 42. The detection circuit 22 then measures a response signal to the drive signal and monitors the changes in the response signal to determine degree of adhesion of the return electrode pad 6.

The response signal (e.g., a returning drive signal) is modified by the impedance of the first and second electrode pads 41 and 42. More specifically, as the impedance between the split electrode pads 41 and 42 changes due to peeling of the return electrode pad 6 from the patient, the detection circuit 22 then supplies the impedance measurement to the controller 24, which determines whether the impedance is within a desired range. If the impedance is outside the desired range an excessive peeling condition exists with the return electrode pad 6 and the controller 24 issues an alarm and/or adjusts the output of the generator 20 (e.g., terminates RF energy supply).

Figure 3:
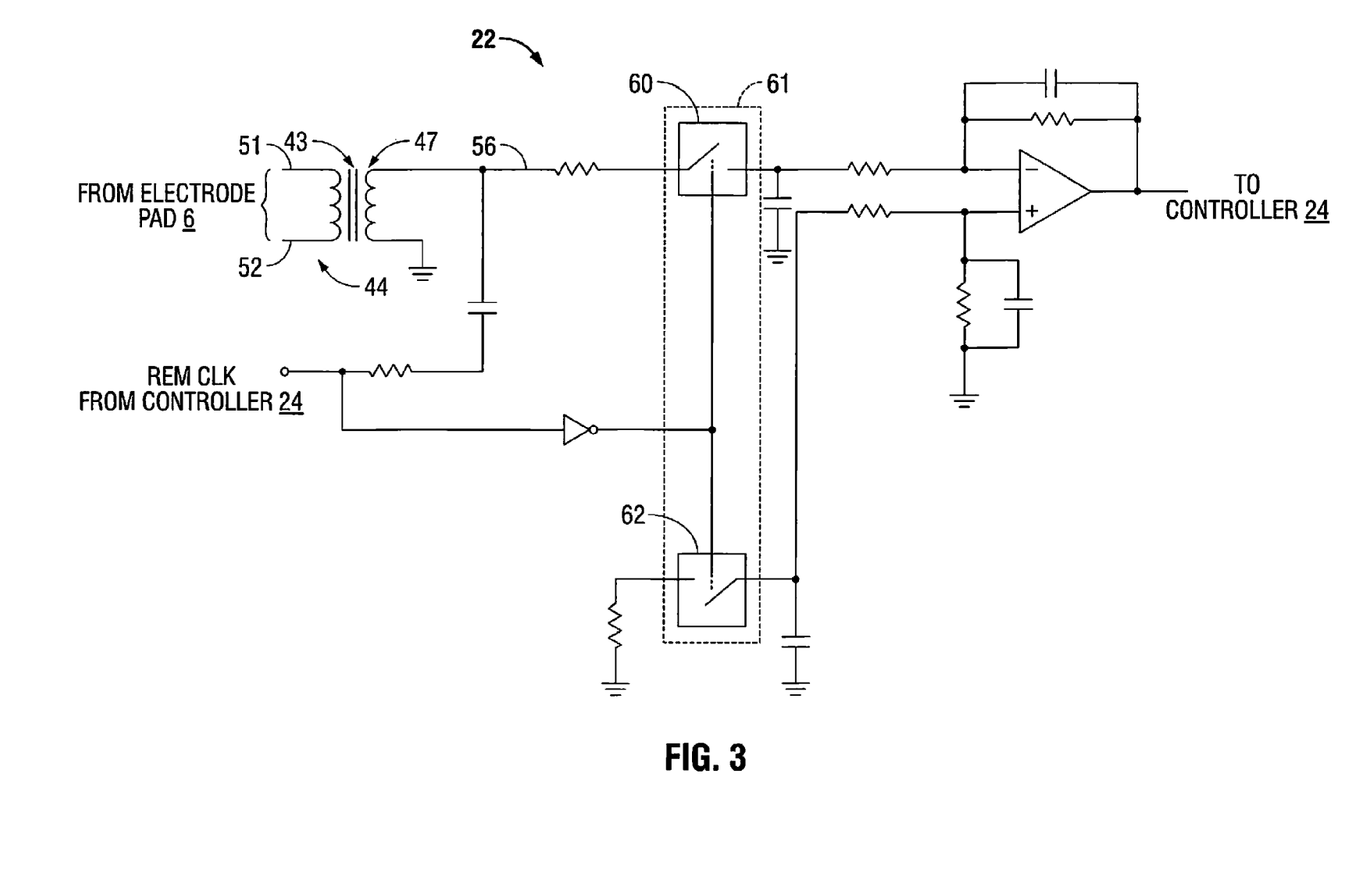
FIG. 3 is a schematic circuit diagram of a detection circuit according to another embodiment of the present disclosure.

With reference to FIG. 3, the exemplary detection circuit 22 is coupled to the primary winding 47 of the transformer 43 and the secondary winding 44 is coupled to the return electrode pad 6. The primary winding 47 is in a single-ended primary configuration, in which the primary winding 47 is referenced to the ground and includes a single-ended line 56. The primary winding 47 is also coupled to an input from the controller 24 for transmitting the REM CLK signal therethrough.

The detection circuit 22 also includes a first switch 60 and a second switch 62 that are operated by the REM CLK. The first and second switches 60 and 62 are analog switches disposed on the same switch package 61 (e.g., being disposed on a single die). The first switch 60 is coupled to the single-ended line 56 of the primary winding 47. The switches 60 and 62 are operated at the REM CLK frequency. When the first switch 60 is open the REM sense signal from the electrode pad 6 is transmitted therethrough to the controller 24. The second switch 62 is neutrally-referenced to a ground and when the second switch 62 is open, only the noise introduced by charge injection is produced. The first and second switches 60 and 62 may be transistors, such as complementary metal-oxide-semiconductor field-effect transistors (CMOS), metal-oxide-semiconductor field-effect transistors (MOSFET), junction field-effect transistors (JFET) and the like.

In essence, a properly designed and functioning return electrode pad utilizes minimal surface area at the contact site, while at the same time, safely returning enough energy to maximize the electrosurgical performance. In one embodiment, temperature performance of a return electrode is measured by applying continuous current for a certain period of time. The final maximum temperature is then recorded for that particular return electrode pad configuration or model. For example, a typical 3 cm single electrode ablation is activated for 12 minutes at a 50% duty cycle (i.e., about 10 sec on and 10 sec off). By utilizing a 30 minute continuous benchmarking method, the return electrode is constrained to a design that is much bigger than needed for most cases. Alternatively, a safety system of the generator terminates energy delivery sooner than actually necessary.

Figure 4:
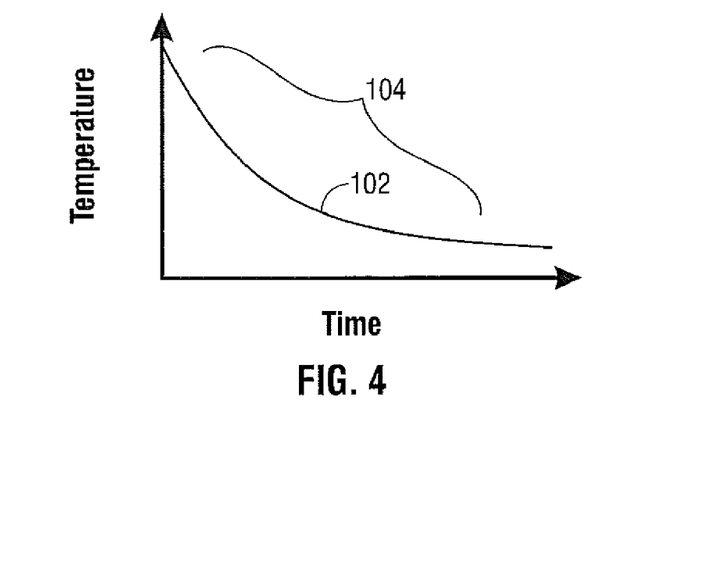
FIG. 4 is a graphical representation of Newton's Law of Cooling.

In embodiments, the temperature of a cooling object can be calculated, at a given time, by using Newton's Law of Cooling. As shown in FIG. 4, a temperature curve 102 shows temperature gradually decreasing, within region 104, while time increases. Newton's Law of Cooling equation is normally expressed as the following first order linear differential equation:

$$dT/dt = -k(T-S) \quad (1)$$

where, "k" is a constant specific to the medium (e.g., tissue at the return electrode pad site) and object (e.g., return electrode pad), "T" is the temperature of the return electrode pad itself, and "S" is the temperature of the tissue at the return electrode pad site surrounding the return electrode pad.

The continuous solution to equation (1) is the following equation:

$$T(t) = S + (T_0 - S)e^{-kt} \quad (2)$$

where, "T(0)" is equal to "$T_0$" (i.e., an initial temperature) and "t" is real-time temperature.

Equation (2) can also be represented in the following discrete form:

$$(T_{n+1} - T_n)/\Delta t = -k(T_n - S) \quad (3)$$

where, "k" is a constant specific to the tissue at the return electrode pad site and return electrode pad, "$T_n$" is the calculated temperature of the return electrode pad, "$T_{n+1}$" is the next calculated temperature of the return electrode pad, "$\Delta t$" is the elapsed time between the calculation of "$T_{n+1}$" and "$T_n$," and "S" is temperature of the tissue at the return electrode pad site.

The discrete solution to equation (3) gives the following equation:

$$T_{n+1} = T_n - k*\Delta t(T_n - S) \quad (4)$$

Accordingly, the temperature of the tissue at the return electrode pad site, i.e., "S" of equation (4), can be dynamically calculated by the generator, thus predicting the temperature of the tissue of a patient underneath a return electrode pad.

Figure 5:
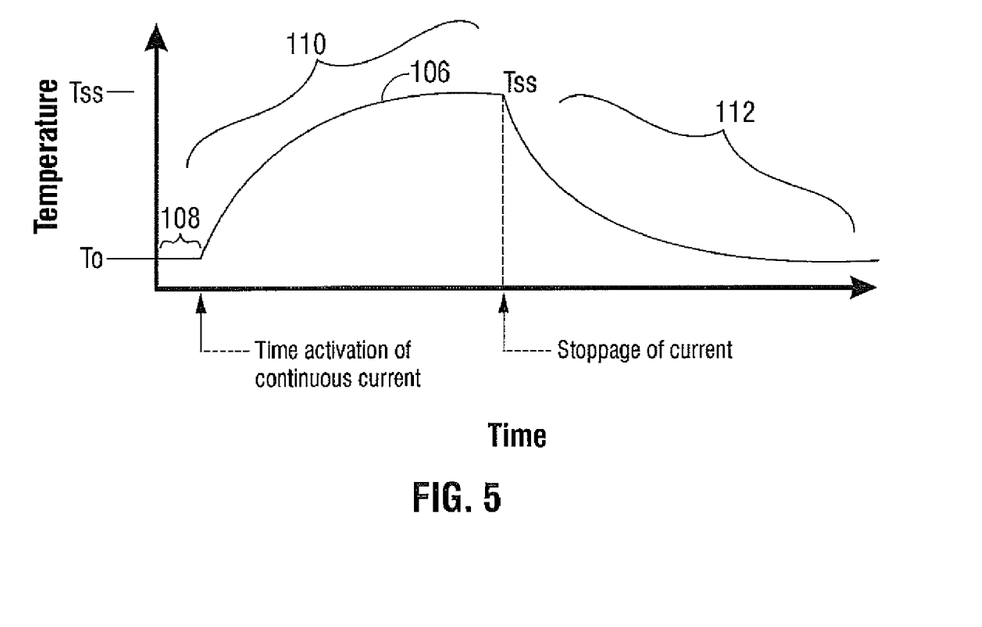
FIG. 5 is a graphical representation of a temperature curve showing the temperature change over time.

FIG. 5 is a graphical representation of a temperature curve 106 showing the temperature of the return electrode pad varying through regions 108, 110, and 112. In region 108, temperature curve 106 is shown having a constant temperature, since no activation of energy is taking place. In region 110, temperature curve 106 gradually increases, from an initial temperature "$T_0$," when a continuous current is activated by a clinician and/or a generator. When temperature curve 106 reaches a steady-state temperature "Tss," temperature curve 106 stops increasing and levels off at a constant rate (i.e., a constant temperature). Subsequently in region 112, temperature curve 106 gradually decreases since the continuous current has been terminated, thus no heat is being generated.

For a given return electrode pad design, there is a continuous applied current level and set of external conditions that produce a unique steady-state temperature "$T_{ss}$" of the return electrode pad. External conditions may include variables that affect the temperature of the return electrode pad, for example, but not limited to, room temperature, body temperature, vascular condition underneath or about the return electrode pad, location and position of the return electrode, thickness of body fat layer, and exposure to the environment. That is, steady-state temperature "$T_{ss}$" is the temperature between the input temperature created by a current load balanced by the external conditions that contribute to removing heat from the return electrode pad.

The above-described factors dictates the following equation:

$$T_{n+1} = T_n - k*\Delta t(T_n - T_{ss}) \quad (5)$$

Equation (5) may be implemented by the embodiments of the present disclosure, by dynamically calculating steady-state temperature "$T_{ss}$" based on applied current and near-worse case external conditions. Equation (5), which may used to calculate steady-state temperature "$T_{ss}$," may be experimentally determined and the results may be subsequently recorded into a look-up table, which may be implemented with the generator. Initial results suggest that equation (5) takes the form of a one-sided quadratic equation, as shown in the following form:

$$Ai^2 + Bi + C \quad (6)$$

where, i>0 and represents the applied current.

Equation (6) corresponds well with equation (7), as shown below, for resistive power dissipation in the form of heat:

$$Power = i^2 R \quad (7)$$

Resistive power dissipation (i.e., equation (7) combined with equation (5)) produces the following equation:

$$T_{n+1} = T_n - k*\Delta t(T_n - (Ai^2 + Bi + C)) \quad (8)$$

In embodiments, equation (8) may be customized for each patient at any time. For example, some variables that may affect equation (8) are the sex of the patient (i.e., male or female) and body fat percentage and/or body mass index (BMI). When these variables are implemented into equation (8), a maximum temperature of the return electrode pad is calculated according to an individual patient (i.e., a maximum temperature prediction).

For example, there are several different variables that may affect steady-state temperature "$T_{ss}$," and a constant "k" specific to a patient or tissue at the return electrode pad site. As discussed above, some of these variables may include sex, body fat percentage, or BMI, muscle mass, vascular conditions, and placement of electrode on specific regions of the body.

By inputting patient data into the algorithm, such as height, weight, and sex, a temperature prediction equation can be calculated specific to a particular patient. For example, for patients with a higher BMI, the equation would have higher values for constant "k" and steady-state temperature "$T_{ss}$."

Figure 6:
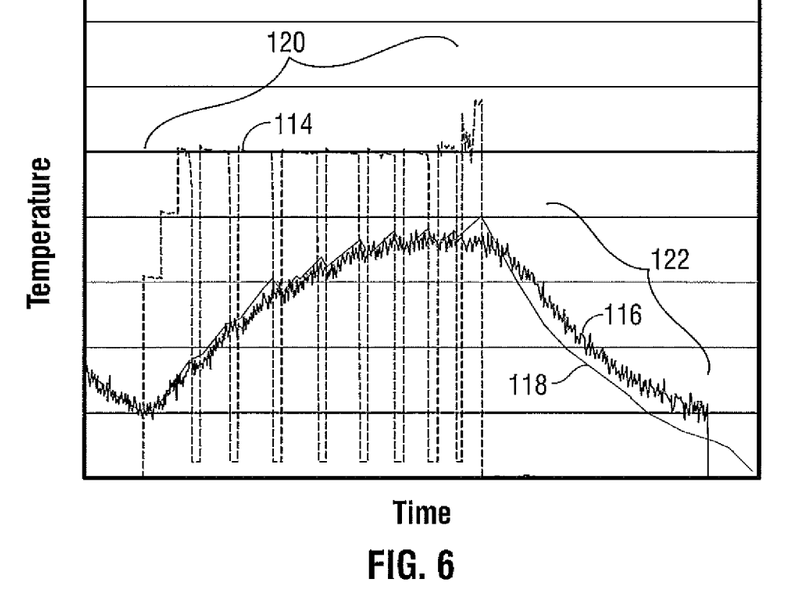
FIG. 6 is a graphical representation of a pulse train of applied current, an actual temperature curve, and a predicted temperature curve.

FIG. 6 is a graphical representation of a pulse train of applied current 114, an actual temperature curve 116, and a predicted temperature curve 118. In region 120, the applied current 114 continuously pulses for a certain time interval, thus generating a pulse train. While applied current 114 is activated by a clinician and/or generator, actual temperature curve 116 gradually increases and then starts leveling off towards the end of region 120. Subsequently in region 122, when applied current 114 is terminated by the generator, actual temperature curve 116 gradually decreases over time in a similar fashion to region 112 of FIG. 5. As shown in FIG. 6, predicted temperature curve 118 is calculated to be very similar to actual temperature curve 116.

Figure 7:
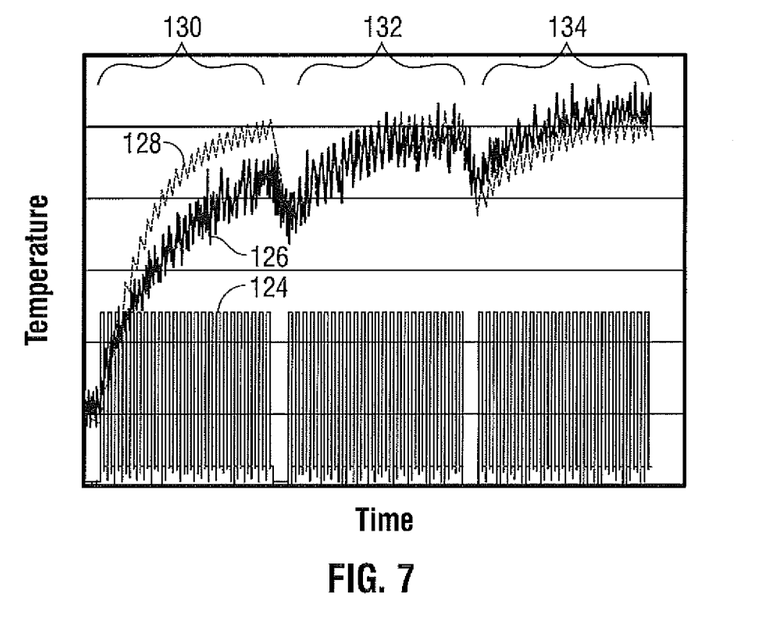
FIG. 7 is a graphical representation of a plurality of pulse trains of applied current, an actual temperature curve, and a predicted temperature curve.

FIG. 7 is a graphical representation of a plurality of pulse trains of applied current 124, an actual temperature curve 126, and a predicted temperature curve 128. In regions 130, 132, and 134, applied current 124 continuously pulses for a certain time interval, which, in turn, causes actual temperature curve 126 to increase over the duration of applied current 124. Between each of the regions 130, 132, and 134, applied current 124 is briefly terminated, which, in turn, causes actual temperature curve 126 to decrease briefly. As shown in FIG.

7, predicted temperature curve 128 is calculated to be very similar to actual temperature curve 116.

Alternatively, the system may be configured to measure body fat percentage based on impedance "Z" between two electrodes and calculate the resulting temperature prediction equation. By measuring impedance "Z", an appropriate temperature prediction equation can be calculated. This equation allows a clinician (i.e., surgeon) greater flexibility in surgical procedures, since the surgical procedure may be conducted without compromising return electrode patient safety.

Figure 8:
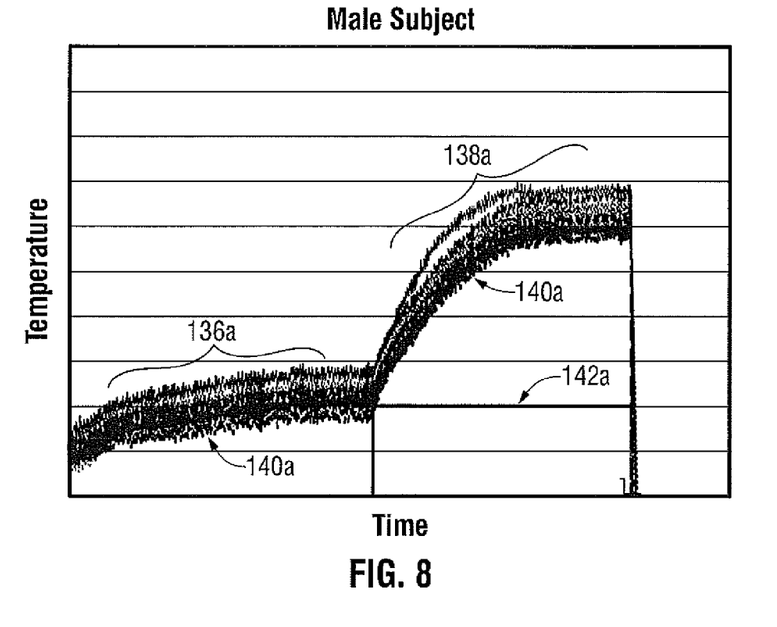
FIGS. 8 and 9 are graphical representations of a plurality of actual temperature curves and a pulse train of applied current between male and female subjects.
Figure 9:
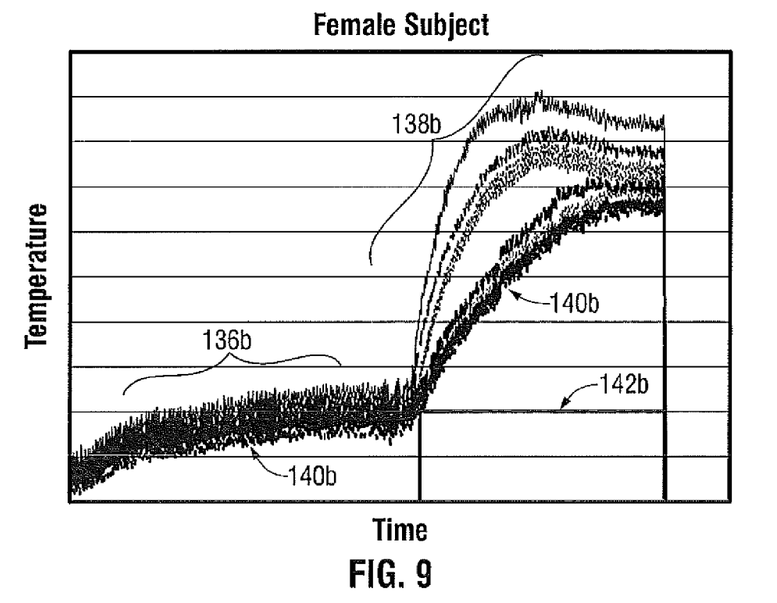

In experiments, as best shown in FIGS. 8 and 9, graphical representations reflect a difference between male and female return electrode heating. In experiments, the applied current was equal and continuous with both male and female subjects. In addition, the activation time for both male and female subjects was about 35 minutes. However, in the experiments the temperature prediction equation was different for both of the subjects. As such, the temperature prediction equation of the female subject required a faster rise time for constant "k" and higher steady state temperature "$T_{ss}$" than the temperature prediction equation of the male subject.

As shown in FIGS. 8 and 9, a plurality of actual temperature curves 140a and 140b and a continuous pulse of applied current 142a and 142b are illustrated. More particularly, FIG. 8 illustrates temperatures curves 140a from a male subject and FIG. 9 illustrates temperature curves 140b from a female subject. In regions 136a and 136b, the temperature curves 140a and 140b increased at substantially constant rate, due to external conditions, until a continuous pulse of applied current 142a and 142b was applied. As shown in regions 138a and 138b, applied current 142a and 142b caused the temperature curves 140a and 140b to rapidly increase until applied current 142a and 142b was terminated. The slope and rate of change in the temperature curves 140a and 140b, within regions 138a and 138b, were different between male and female subjects. Thus, illustrating the difference in male and female characteristics.

Figure 10:
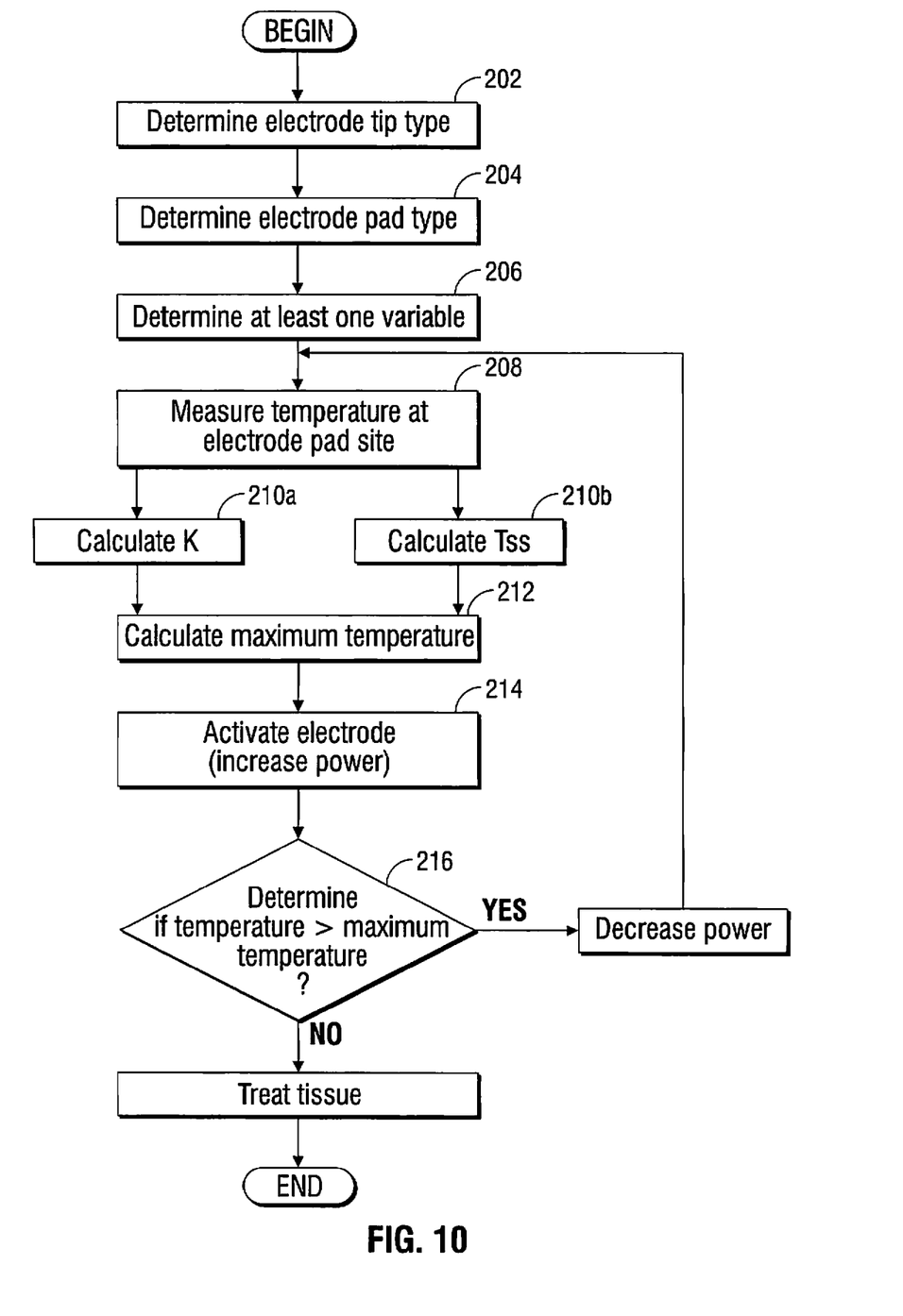
FIG. 10 is a schematic block diagram of an algorithm for calculating a maximum temperature.

FIG. 10 depicts a method for calculating a maximum temperature at a surgical site according to an embodiment of the present disclosure. The method may be embodied as a software application embedded in the memory 26 and executed by the microprocessor 25 to the energy output of control generator 20. The method utilizes a temperature predicting circuit 23 which can be implemented in a closed-loop control scheme as part of the sensor circuit 22. As mentioned above, to maintain a "safe" temperature at the return electrode pad site, the temperature should be kept at a temperature less than the maximum temperature calculated.

In step 202, an electrode tip 2a of instrument 2 is connected and may be detected by the electrosurgical system or algorithm 200. A clinician may manually enter the type of electrode tip 2a utilized in a surgical procedure, or, in the alternative, generator 20 may automatically detect the electrode tip 2a being utilized. In the case where the electrode tip 2a is detected by the system 200, the system 200 may load values or variables from a look-up table pertaining to the type of electrode tip 2a being utilized. In addition, the system 200 may adjust any settings due to the type of electrode tip 2a being utilized.

In step 204, a return electrode pad 6 may be detected by the generator 20. Similarly to the electrode tip 2a, a clinician may manually enter the type of return electrode pad 6 being utilized in a surgical procedure, or, in the alternative, generator 20 may automatically detect the return electrode pad 6 being utilized. For example, the size, weight, and material of the electrode pad 6 may have a set of values that may be detected by the generator 20. Alternatively, a look-up table may include a certain model number of the return electrode pad 6 and then calibrate the generator 20 to accept and configure the return electrode pad 6.

In embodiments, the generator 20 may include safety features in the event that an incorrect setting is entered by a clinician or the system 200 and/or in the event that a mislabeled and/or improper return electrode pad 6 is connected to the generator 20. That is, the safety features of the generator 20 may warn the clinician by way of an alarm, light, and/or simply terminate the supply of energy to the electrode tip 2a of the electrosurgical instrument 2. The safety features may include, but are not limited to, one or more sensors, feed-back loop algorithms, or the like.

In step 206, one or more variables may be determined by the generator 20 with regard to a specific patient and/or environment that the return electrode pad 6 is attached thereto. For example, one variable may be type of patient, for example, but not limited to, sex, body weight, body mass index (BMI), and body fat percentage. Other suitable variables contemplated may be inputted into the system and/or detected by the system, for example, but not limited to, humidity of the operatory and temperature of the operatory, In step 210a, a constant "k" is calculated by the system that is specific to the return electrode pad 6 or skin of patient. It should be noted that in this, or any other suitable step, "A," "B" and "C" of equations (6) and (8) may be calculated or found on a look up table. In step 210b, a final temperature "$T_{ss}$," is calculated. Steady state temperature "$T_{ss}$" is the temperature the input of heat created by the current and is balanced out by the external forces removing the heat.

In step 212, system 200 calculates (i.e., predicts) a next maximum temperature "$T_{n+1}$" by utilizing equation (8), as described above and shown below.

$$T_{n+1}=T_n-k*\Delta t(T_n-(Ai^2+Bi+C)) \quad (8)$$

Alternatively, system 200 may calculate the maximum temperature "$T_{n+1}$" by utilizing equation (5) described above. In order to effectively calculate the maximum temperature prediction "$T_{n+1}$," the constant "k" from step 210a and maximum temperature prediction "$T_{ss}$" from step 210b is previously calculated and then implemented into equation (5) to calculate the maximum temperature prediction "$T_{n+1}$."

In step 214, the electrode tip 2a is activated by a clinician to treat a patient. In this step 214, any suitable treatment may be performed, such as, for example, ablation, cauterization, and/or desiccation.

In step 216, the real-time temperature "$T_{real}$" may be determined by any suitable sensor disposed on or about the electrode tip 2a. Additionally or alternatively, an additional (or the same sensor) may be placed on the return electrode pad 6. The real-time temperature "$T_{real}$" is the temperature of the return electrode pad 6. If the real-time temperature "$T_{real}$" is greater than or equal to the predicted maximum temperature "$T_{n+1}$," the power (i.e., energy) is decreased at the electrode tip 2a (e.g., current or voltage) to avoid any injury (e.g., burning) to the patient at the return electrode pad site. At the same time the feed-back loop reverts back to step 208 to measure the real-time temperature "$T_{real}$." In embodiments, the feed-back loop may measure the real-time temperature "$T_{real}$" continuously (i.e., at all times). Alternatively, the feed-back loop may measure the real-time temperature at a predetermined or real-time adjustable time interval (e.g., 1 second interval, 30 second interval, or 1 minute interval).

Alternatively, if the real-time temperature "$T_{real}$" is less than the maximum temperature "$T_{n+1}$," then treatment to the tissue of the patient (e.g., ablation, coagulation, or desiccation) is continued until treatment is complete at the surgical site. At substantially the same time, the feed-back loop reverts back to step 208 to measure the real-time temperature "$T_{real}$" at the return electrode pad site.

Additionally or alternatively, in any of one of the above-discussed embodiments, the temperature may be calculated based on current, time, and/or patient factors, instead of measuring the temperature with customary temperature sensors.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator for supplying electrosurgical energy to tissue, the electrosurgical generator comprising:
    sensor circuitry coupled to at least one return electrode pad and configured to determine tissue temperature at a return electrode pad site;
    a processing device configured to determine a maximum temperature of tissue at the return electrode pad site based on at least one characteristic of a patient; and
    a controller configured to regulate output of the electrosurgical generator based on the tissue temperature and the determined maximum temperature.

2. The electrosurgical generator according to claim 1, wherein the sensor circuitry is further configured to measure impedance at the at least one return electrode pad to determine the at least one characteristic of a patient.

3. The electrosurgical generator according to claim 1, wherein the controller is configured to adjust the output of the electrosurgical generator to a predetermined level based on the determined maximum temperature.

4. The electrosurgical generator according to claim 1, wherein the processing device is configured to determine a type of the at least one return electrode pad.

5. The electrosurgical generator according to claim 4, wherein variables from a look-up table are loaded into the electrosurgical generator and the processing device automatically adjusts the energy based on the type of return electrode pad.

6. The electrosurgical generator according to claim 1, wherein the at least one characteristic of the patient is selected from the group consisting of sex, body weight, body mass index, and body fat percentage.

* * * * *